US007793658B2

(12) United States Patent
Stratton

(10) Patent No.: US 7,793,658 B2
(45) Date of Patent: Sep. 14, 2010

(54) PERSONAL ASSISTIVE BREATHING APPARATUS

(75) Inventor: Kelsey Stratton, Lincoln, MA (US)

(73) Assignee: Go2 LLC, Lincoln, MA (US)

( * ) Notice: Subject to any disclaimer, the term of this patent is extended or adjusted under 35 U.S.C. 154(b) by 1019 days.

(21) Appl. No.: 11/465,902

(22) Filed: Aug. 21, 2006

(65) Prior Publication Data

US 2008/0041375 A1 Feb. 21, 2008

(51) Int. Cl.
*A61M 15/08* (2006.01)
*A61M 15/00* (2006.01)

(52) U.S. Cl. ............................ 128/203.23; 128/203.12

(58) Field of Classification Search ............ 128/204.18, 128/205.24, 205.25, 200.24, 203.24
See application file for complete search history.

(56) References Cited

U.S. PATENT DOCUMENTS

| | | | | |
|---|---|---|---|---|
| 3,186,407 | A | 6/1965 | Morrison | |
| 3,770,170 | A * | 11/1973 | Hayes | 222/402.11 |
| 4,119,097 | A | 10/1978 | Spector | |
| 4,582,054 | A | 4/1986 | Ferrer | |
| 4,637,387 | A | 1/1987 | Hall | |
| 4,669,462 | A | 6/1987 | Marshall | |
| 5,429,125 | A | 7/1995 | Wagner et al. | |
| D411,101 | S | 6/1999 | Stickney | |
| 5,979,442 | A | 11/1999 | Orr | |
| 6,125,844 | A | 10/2000 | Samiotes | |
| 6,247,471 | B1 | 6/2001 | Bower et al. | |
| 6,557,549 | B2 | 5/2003 | Schmidt et al. | |
| 6,708,692 | B2 * | 3/2004 | Lee et al. | 128/205.24 |
| D492,771 | S | 7/2004 | King et al. | |
| D492,993 | S | 7/2004 | King et al. | |
| D492,994 | S | 7/2004 | King et al. | |
| D493,222 | S | 7/2004 | King et al. | |
| 6,837,245 | B2 | 1/2005 | Matheny et al. | |
| 6,848,443 | B2 | 2/2005 | Schmidt et al. | |
| 7,341,056 | B1 * | 3/2008 | Tucker | 128/200.14 |
| 2001/0020470 | A1 | 9/2001 | Zupan | |
| 2001/0035435 | A1 * | 11/2001 | Nakamura et al. | 222/402.13 |
| 2002/0050275 | A1 * | 5/2002 | Koch | 128/204.18 |
| 2005/0284896 | A1 * | 12/2005 | Jaworski et al. | 222/402.1 |
| 2006/0011196 | A2 * | 1/2006 | Gallem et al. | 128/200.24 |
| 2006/0231580 | A1 * | 10/2006 | Lawson et al. | 222/519 |

OTHER PUBLICATIONS

Pictures—Aug. 29, 2006 www.oxia.com (http://secure.bbdesign.com/oxia/art/ph_container3.jpg)(p. 1).
Article—Aug. 29. 2006 www.oxia.com /news_detail.aspx?view+9) pp. 1 and 2.
Picture—BlueAir 2L—Aug. 29, 2006 http://betterthanair.stores.yahoo.net/blueair21.html (p. 1).
Picture—BlueAir—http://betterthanair.stores.yahoo.net/cano2ox.html (p. 1 and 2).
Picture—Product 'O' 'O2go'—http://betterthanair.stores.yahoo.net/productoo2go.html (p. 1).
Picture—HangOverAir—http://betterthanair.stores.yahoo.net/hangoverair.html (p. 1).

* cited by examiner

*Primary Examiner*—Tatyana Zalukaeva
*Assistant Examiner*—Rachel T Young
(74) *Attorney, Agent, or Firm*—Lackenbach Siegel, LLP; Andrew F. Young

(57) ABSTRACT

The present invention relates to a personal use assistive breathing device wherein a can adaptor or bottle mounting member is secured to a bottle canister containing a pressurized gas. A mouth piece member retains an action knob positioned for actuating a stem valve on the bottle canister upon a rotation. During use the action knob is spaced away from the mouthpiece and air passages entrain ambient atmospheric air with the escaping pressurized gas. The action knob may be retained in the in-use position without continual pressure allowing hands-free use. During storage, the action knob is spaced in contact with the mouthpiece prohibiting unintended gas release and enabling ready handling without risk of gas-loss.

21 Claims, 8 Drawing Sheets

100
101
102

100
101
105
103
108
106
X
104
107
109
102

Fig. 3
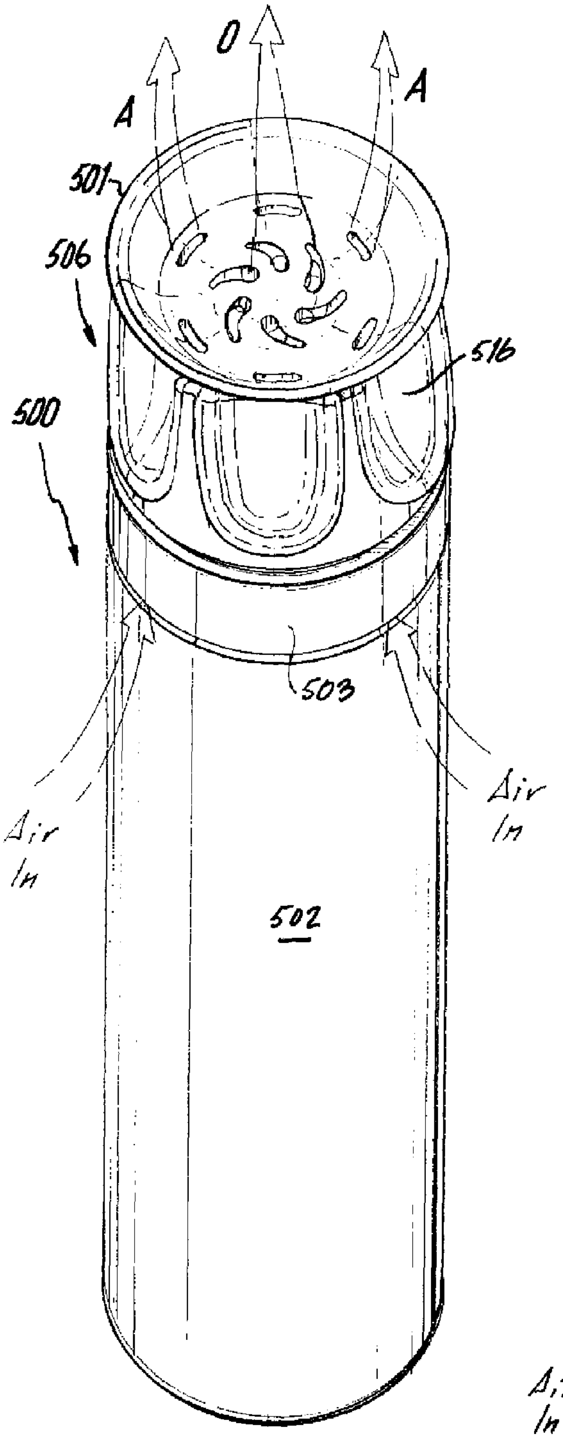
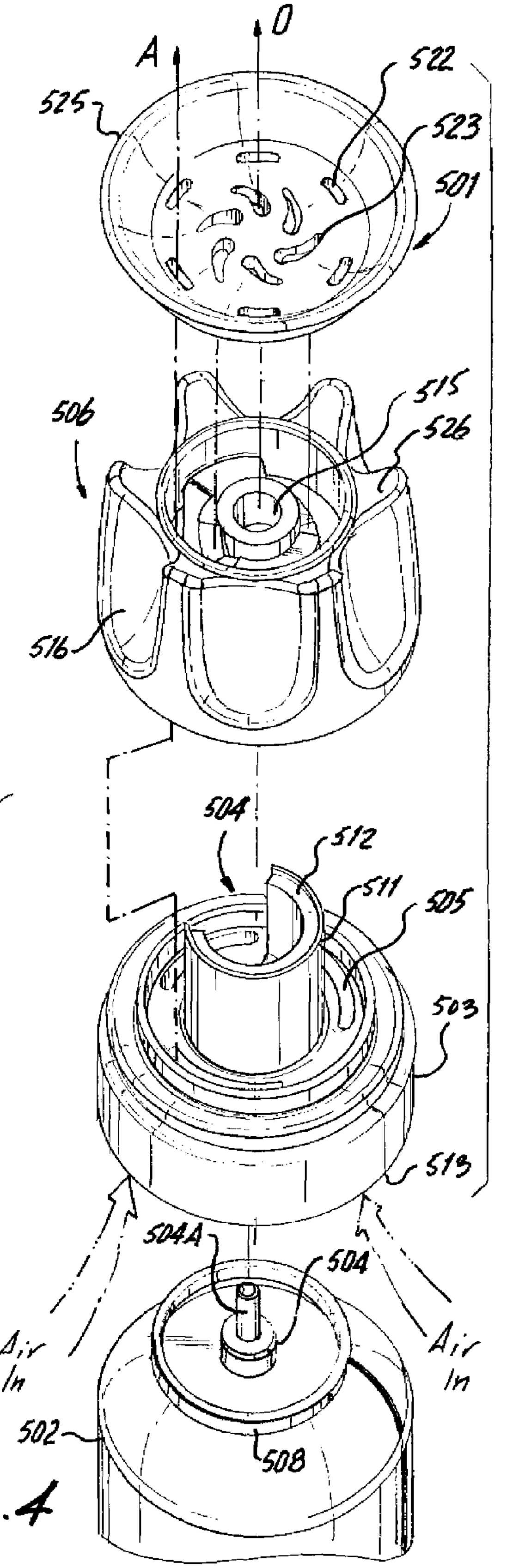
Fig. 4

Fig. 5
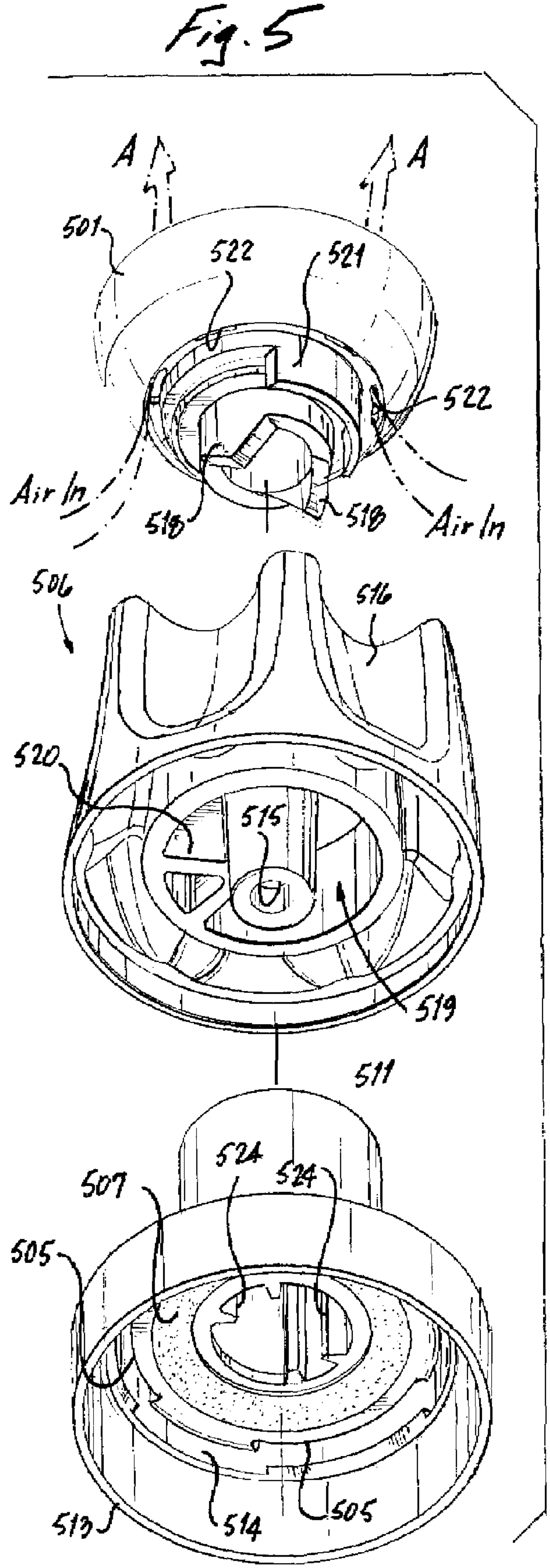
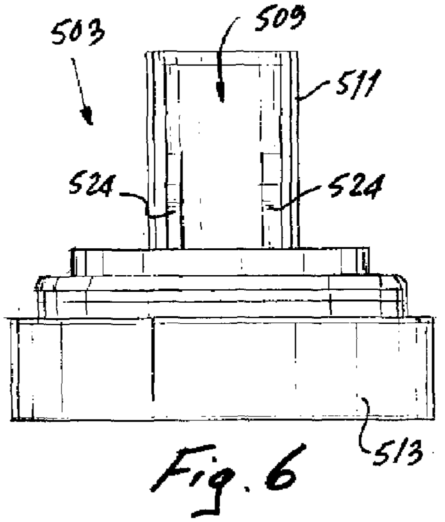
Fig. 6
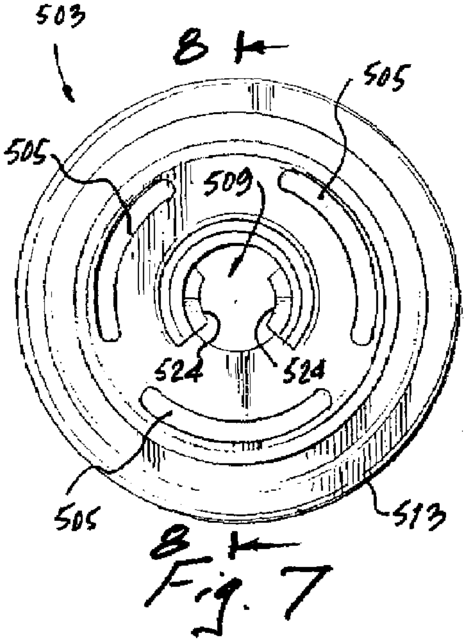
Fig. 7
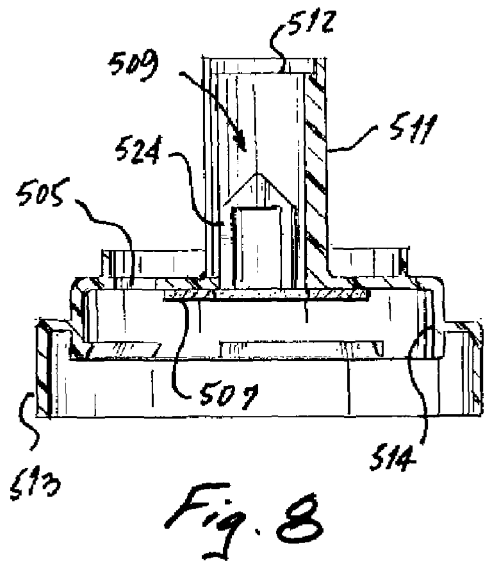
Fig. 8

Air In
501
506
521
511
A
0
519
518
517
D
K
504A
523
522
513
503
502
R'
R

PERSONAL ASSISTIVE BREATHING APPARATUS

BACKGROUND OF THE INVENTION

1. Field of the Invention

The present invention relates to an assistive breathing apparatus for sports or exercise use. More specifically, the present invention relates to a breathing apparatus that employs a unique and secure motion for releasing stored gas and supplying both the stored gas and entrained ambient atmosphere to a user while enabling later secure storage without risk of unintended release.

2. Description of the Related Art

The related art involves a wide number of personal use air canisters or oxygen canisters that often include some form of mouth-mask or lip canister. Personal-use oxygen canisters are commonly used, for example to augment or assist blood-oxygen content during extreme sports activity or during a user's presence at a high-altitude/low oxygen partial-pressure condition, where recovery of blood-oxygen content is a slow process.

The use of oxygen canisters has been long known from high-altitude mountaineering and often these canisters are strapped to a users back like a back-pact, with a flexible hose and separate mask used to provide oxygen to a user's lip region. Such uses have fallen-out of favor unless mandatory due to the detrimental weight and awkward positioning required. It is also known, for example to employ a small-sized oxygen canister with a mouthpiece projecting at a right-angle to the canister axis and a twist-opening valve. With these constructions, a plurality of fixing or positioning straps are employed to elastically fix the mouthpiece to the user's lip region, with the long-axis of the bottle projecting along the user's chest. These constructions are disfavored due to their interference with close body positioning (for example during rock climbing), and the uncomfortable pressure applied to the user's lips and mouth.

Referring now to FIGS. 1 and 2, a conventional personal assistive apparatus 100 includes a bottle member 102 joined to a universal mouthpiece member 103 having a single gas opening 105 positioned centrally. A cover cap member 101 is fittable over both bottle ember 102 and universal mouthpiece member 103 and outer surface portion 107 of bottle 102.

In a pre-use condition, a male valve stem member 104 projects upwardly from a valve stem assembly region on bottle 102 and is partially received within a nesting flange 106 projecting centrally from within mouthpiece member 103. An enclosed passage (not shown) projects from nesting flange member 106 to single gas opening 105 to transfer use-gas directly to a user during a use. Valve stem member 104 is actionable, and will release use-gas, only along an axial motion along the length of valve stem member 104. As a consequence, in a pre-use position mouthpiece member 103 rests over valve stem member 104 without contacting outer surface portion 107 of bottle 102 and is solely suspended upon valve stem member 104. As a consequence, an outer and bottom-most lip portion 108 of universal mouthpiece member 103 fails to contact bottle member 102 and is pivotal relative thereto. In this pre-use storage position, cap member 101, having a larger inner diameter than an outer diameter of universal mouthpiece member 103 may cover member 103 and a bottom portion of cap member 101 may snap-engage a detent ring 109 to retain cover member 103 within the bounded volume defined therein.

As an unfortunate result of this universal design, it is common during shipping a pre-use for universal mouthpiece member 103 to become disengaged with valve stem 104 and to rattle within snap-engaged cap member 101, thereby requiring re-attachment and often hand-steadying by a user prior to a use. In an in-use position, a user positions universal mouthpiece member 103 about valve stem 104 and uses a first hand to grip a barrel of bottle 102 and a second hand to steady universal mouthpiece member 103 to position the same about a lip region. To initiate a use, a user presses bottle 102 against their lip region steadying respectively with their hands. As pressure is applied, nesting flange 106 presses downwardly on valve stem 104 and actuates release of use-gas. In a full-use position, bottom-most lip portion 108 will contact outer surface portion 107 and prevent over-compression of the valve. Also in full-use position, a sealing flange on universal mouthpiece member 103 fully seals about the user's lip region to prevent unintended escape of use gas. Upon a release of the pressure, valve stem 104 pushes mouthpiece member 103 away from surface portion 107. As a consequence, mouthpiece member 103 is now only centrally-supported and may pivot and tilt relative to bottle 102, and may easily become disengaged and fall away without two-handed use. While this central-support of mouthpiece 103 enables its use on a number of canisters or bottles 103, hence its universal capacity, this very construction raises substantive detriments.

In sum, as is obvious from this conventional construction, there are substantive including risk of damage to valve stem member 104 through pivot and miss-position of mouthpiece member 103. A related detriment is the unintended separation and potential loss of mouthpiece member 103 fully from assembly 100 upon removal of cover cap 101. An additional detriment is the requirement for both (a) dual-handed use to operate securely, (b) the requirement for continual hand pressure along the bottle axis to actuate the valve assembly, and the inability to use personal assistive apparatus 100 in a hands-free condition, for example while resting. As a consequence, the detriments of assembly 100 prohibit its use during high-energy sports such as climbing, mountaineering, and extreme skiing.

Such related art liners are also shown at BetterThanAir, LLC of Evergreen, Colo. 80437 and its related website, and at Oxia Distribution Inc. of Snowmass, Colo. 81654 and its related website. Alternative attachment mechanisms include a threaded container attachment, for example in U.S. Pat. No. 3,186,407 to Morrison.

What has also recently been appreciated by those of skill in the art is the prohibitive focus on supplying a user's lung gas volume solely from the attendant canister. Where a mouthpiece is sealed to a user's lip region, a normal inhalation may have a volume of 2.5 liters requiring the same delivery from the limited-use canister. The supply of such large volumes of gas to satisfy a user's lung volume requires the use of large canisters or heavy canisters to withstand increased internal pressure. Thus, while the sports-need is to augment blood-oxygen content may require only the supply of pure oxygen, the parallel need to satisfy lung volume often requires the use of pressurized breathing air. Now, that sports medicine recognizes the dangers of oxygen-poisoning (where the blood is over-oxygenated causing damage), it is critical to avoid the risks existent with pure oxygen. In sum, a conundrum exists in the industry between the need to supply oxygen and to supply sufficient lung volume to users that is yet unsatisfied in the industry. No response to this need has been satisfactory to date.

As a consequence of the above it is now clear that the related art has failed to appreciate the need for a personal use assistive breathing apparatus having a small size for transport, a securely attached construction to prohibit separation of damage prior to or during storage, and with an optional capacity for hands-free use to allow improved user resting and recovery under extreme conditions, all while avoiding the dangers and risks associated with the related art.

Accordingly, there is a need for an improved personal-use assistive breathing apparatus that overcomes at least one of the detriments noted above.

OBJECTS AND SUMMARY OF THE INVENTION

An object of the present invention is to provide a personal use assistive breathing apparatus that overcomes on of the detriments known above Another aspect of the present invention is to provide a personal use assistive breathing apparatus that employs ambient atmosphere as a beneficial mixing aid to augment released gas volume to satisfy a lung volume need.

Another aspect of the present invention involves the use of a secure triggering or actuation mechanism that enables operation with a single hand and thereafter positioning a mouthpiece in a convenient position, even proximate a user's lip region with a resultant decrease in user lip-region-pressure.

The present invention relates to a personal use assistive breathing device wherein a can adaptor or bottle mounting member is secured to a bottle canister containing a pressurized gas. A mouth piece member retains an action knob positioned for actuating a stem valve on the bottle canister upon a rotation. During use the action knob is spaced away from the mouthpiece and air passages enable an entrainment ambient atmospheric air with the escaping pressurized gas. The action knob may be retained in the in-use position without continual pressure allowing hands-free use. During storage, the action knob is spaced in contact with the mouthpiece prohibiting unintended gas release and enabling ready handling without risk of gas-loss.

According to an embodiment of the present invention there is provided an assistive breathing apparatus for personal use by a user, comprising: a bottle mounting member, means for securely mounting the bottle mounting member about a valve assembly of an external bottle having a bottle axis and containing a use-gas, a mouthpiece member mounted on the bottle mounting member, an action knob pivotally mounted between the bottle mounting member and the mouthpiece member, means for entraining an external atmosphere within a release volume of the use-gas during the use, and means for actuating the valve assembly upon a rotation of the action knob by the user about the bottle axis.

According to another aspect of the present invention there is provided an assistive breathing apparatus for personal use by a user, wherein: the means for securely mounting further comprising: at least one of a means for snap-mounting the bottle mounting member on the bottle and an adhesive joining means for adhering the mounting member on the bottle without actuating the valve assembly.

According to another aspect of the present invention there is provided an assistive breathing apparatus for personal use by a user, wherein: the breathing apparatus includes the means for snap-mounting, and the means for snap-mounting further comprises: at least a first snap link member for snap engaging a rim of the bottle.

According to another aspect of the present invention there is provided an assistive breathing apparatus for personal use by a user, wherein: the breathing apparatus includes the means for snap-mounting, and the means for snap-mounting further comprises: at least the adhesive joining means for adhering.

According to another aspect of the present invention there is provided an assistive breathing apparatus for personal use by a user, wherein: the breathing apparatus includes the means for snap-mounting, and the means for snap-mounting includes both the at least a first snap link member for snap engaging a rim of the bottle and the adhesive joining means for mounting.

According to another aspect of the present invention there is provided an assistive breathing apparatus for personal use by a user, wherein: the means for actuating the valve assembly includes dual rotation means for enabling a rotation of the action knob in either direction about the bottle axis from a non-actuation position to respective dual use positions, thereby improving a user convenience of the apparatus.

According to another aspect of the present invention there is provided an assistive breathing apparatus for personal use by a user, further comprising: means for retaining the valve assembly of the bottle in an in-use hands-free actuation position following the rotation, thereby allowing the apparatus to have an improved user convenience.

According to another aspect of the present invention there is provided an assistive breathing apparatus for personal use by a user, wherein: the means for actuating the valve further comprises: means for bounding and stabilizing a valve stem of the valve assembly during an actuation, whereby the means for bounding and stabilizing minimize a misalignment of the valve stem and damage to the valve assembly.

According to another aspect of the present invention there is provided an assistive breathing apparatus for personal use by a user, further comprising: a plurality of air passages in the mouth piece member, a first portion of the air passages transmitting the use-gas to the user during a personal use, and a second portion of the air passages transmitting the entrained atmosphere to the user from the means for entraining, whereby during the use the user inhales both the use-gas and the entrained atmosphere.

According to another aspect of the present invention there is provided an assistive breathing apparatus for personal use by a user, further comprising: means for guiding the use-gas from the valve assembly to the first portion of the air passages during a use, whereby the means for guiding aids a transportation of the use-gas to the user.

According to another aspect of the present invention there is provided an assistive breathing apparatus for personal use by a user, further comprising: means for sealing the means for entraining the external atmosphere following the use, whereby the means for sealing positions the action knob in close proximity to the mouthpiece member.

According to another aspect of the present invention there is provided an assistive breathing apparatus for personal use by a user, further comprising: a plurality of gripping aids proximate a periphery of the action knob, whereby the gripping aids improve a user-grip of the action knob during the use.

According to another aspect of the present invention there is provided an assistive breathing apparatus for personal use by a user, further comprising: means for sealing the means for entraining the external atmosphere following the use, the means for sealing further comprising: a convex curved sealing surface on the mouthpiece member, and a concaved sealing surface on the action knob, whereby the mouthpiece member nests within the action knob and the action knob moves relative to the sealing surface during the rotation and use.

According to another aspect of the present invention, there is provided a method for assembling an assistive breathing apparatus, comprising the steps of: providing a bottle having a bottle axis and containing a use-gas, providing a bottle mounting member, securing the bottle mounting member about a valve assembly of the bottle, positioning an action knob about a portion of the bottle mounting member, securing a mouthpiece member on the bottle mounting member, thereby enabling a relative rotation of the action knob relative to both the bottle mounting member and the mouthpiece member.

According to another aspect of the present invention, there is provided a method for assembling an assistive breathing apparatus, wherein: the step of securing a mouthpiece member includes a step of: providing a means for actuating a valve assembly of the bottle upon a rotation of the action knob by the user about the bottle to release the use-gas.

According to another aspect of the present invention, there is provided an assistive breathing apparatus, wherein: the step of securing the bottle mounting member includes a step of snap-engaging the bottle mounting member with a rim of the bottle, whereby a positive snap-fit secures the bottle mounting member to the bottle.

The above, and other objects, aspects, features and advantages of the present invention will become apparent from the following description read in conduction with the accompanying drawings, in which like reference numerals designate the same elements.

BRIEF DESCRIPTION OF THE DRAWINGS

FIG. 3 is a perspective assembled view of a personal use assembly according to the present invention.

FIG. 4 is an exploded perspective view of the operative aspects of FIG. 3.

FIG. 5 is bottom side exploded perspective view of selected elements in the present invention.

FIG. 6 is a side view of a mounting adaptor member according to the present invention.

FIG. 7 is a top view of FIG. 6.

FIG. 8 is a sectional view along line 8-8 in FIG. 7.

DETAILED DESCRIPTION OF THE PREFERRED EMBODIMENTS

Figure 1:
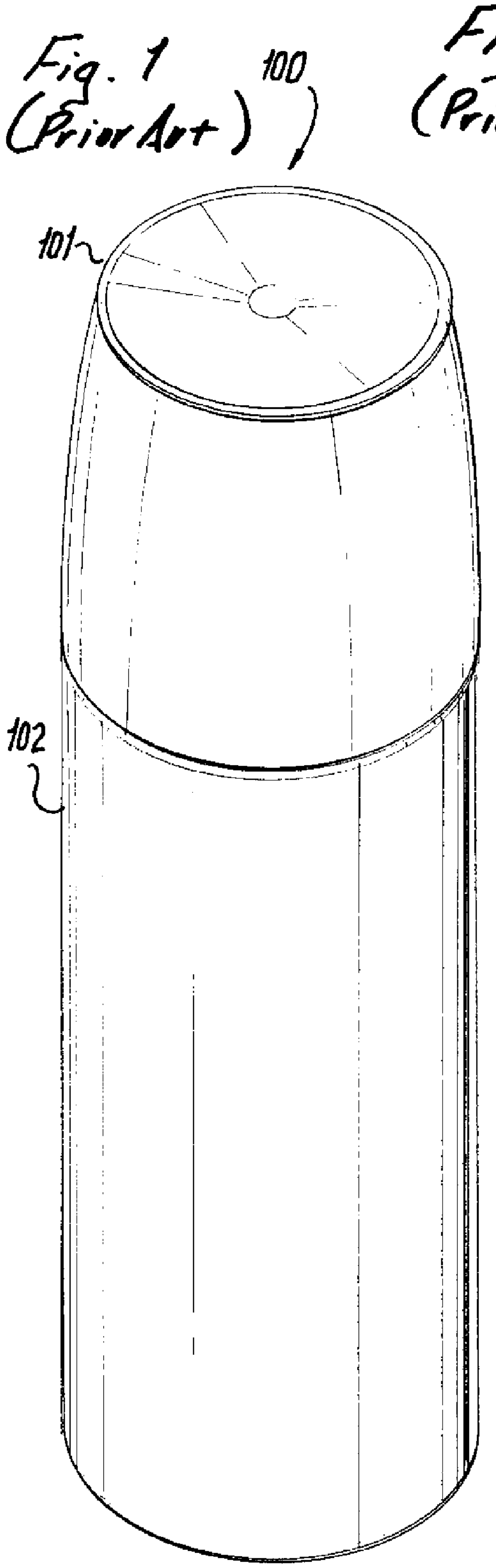
Fig. 1 (Prior Art)
FIG. 1 is a perspective view of a conventional personal use air supply canister assembly.
Figure 2:
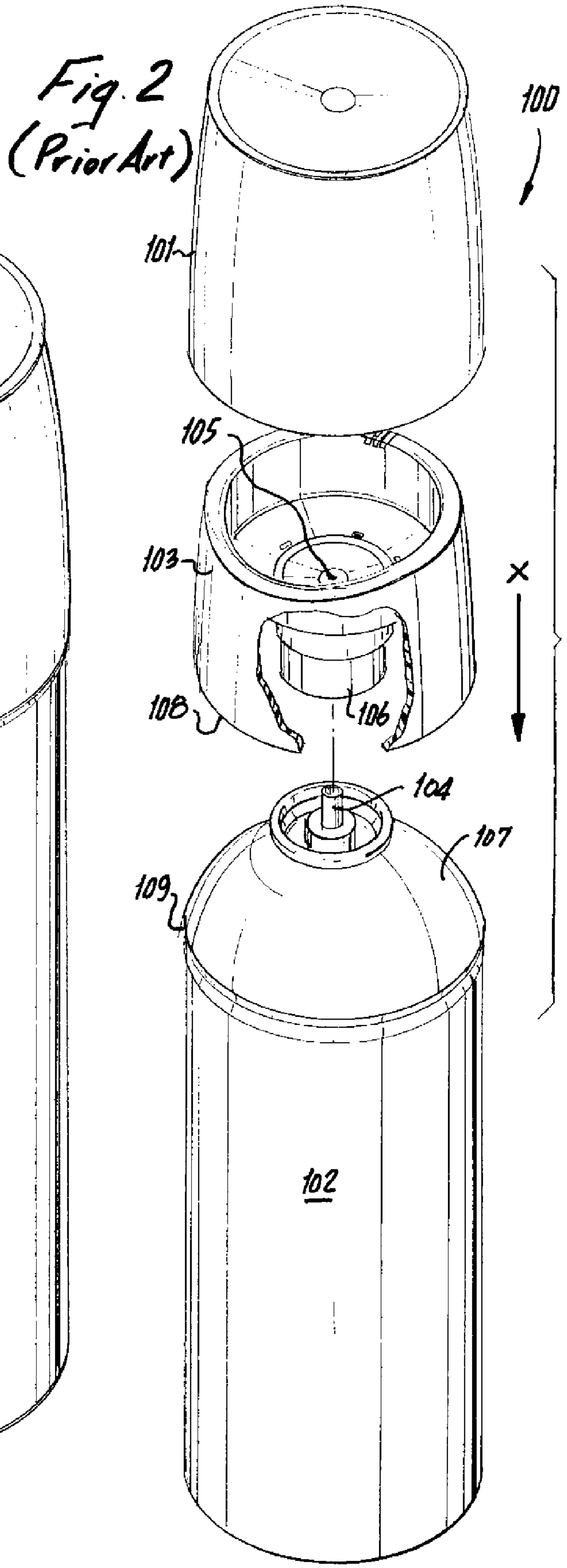
Fig. 2 (Prior Art)
FIG. 2 is an exploded perspective view of the conventional canister assembly of FIG. 1.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale or shape. For purposes of convenience and clarity only, directional terms, such as top, bottom, up, down, over, above, and below may be used with respect to the drawings. These and similar directional terms should not be construed to limit the scope of the invention in any manner. Furthermore, the words "connect," "couple," and similar terms with their inflectional morphemes do not necessarily denote direct and immediate connections, but also include connections through mediate elements or devices.

Referring now to FIGS. 3-4, a personal assistive breathing apparatus 500 includes an assembly fixably joined to a top portion of a gas container 502. The assembly includes a bottle mounting member or can adaptor 503 fixed on a valve boss 508 on a top of gas canister 502, a mouth piece member 501, and a retained action knob member 506 operating there between. As shown, gas canister includes a valve stem member 504A on a valve support or stem support member 504.

Bottle mounting member 503 includes an outer skirt portion 513 for receiving and positioning gas container 502 during an assembly, and is formed in a series of stepped regions, as shown. A plurality of outer base holes 505 are positioned about a mid-region of bottle mounting member 503 for enabling an alternative (non-principal) source of ambient air to a user during a use from a gap between outer skirt member 513 and bottle member, as will be discussed. An inner sleeve member 511 projects upwardly away from outer skirt portion or member 513 and openings 505 and includes therein a top groove 512 formed about a portion of an inner periphery thereof for sealing with mouthpiece member 501, as will be discussed. It should be noted that sleeve member 511 forms a semi-complete arc having a gap about the central axis.

Mouthpiece member 501 includes an outer lip sealing rim 525 and a plurality of outer air flow openings 522 about an outer ring for allowing the flow of ambient air A and a plurality of inner oxygen openings 523 about an inner ring for allowing the flow of oxygen O from bottle 502. As will be appreciated, the bowl defined by rim 525 when positioned on a user's lips aids the mixing of ambient air A and supplied oxygen O proximate a user's mouth.

Action knob 506 includes a plurality of outer periphery undulations 516 for improving a grip during rotation relative to bottle 502, as will be discussed. Also noted is the formation of a receiving bowl curve 526 formed proximate top portions of respective undulations 516 to match a bottom curve of mouthpiece member 501, as will be shown. An inner central opening 515 provides for the flow of oxygen O from valve stem member 504A through sleeve member 511 to inner openings 523.

Referring now to FIGS. 5-8 assembly members are positioned for review. Mouth piece member 501 includes a gluing or fixing assist member 521 projecting downwardly parallel to a bottle central axis for engaging a respective gap formed in sleeve member 511, described above. As noted best in FIG. 8, top groove 512 in sleeve 511 engages a ring edge projecting from a bottom of mouthpiece 501 concurrent with glue ember 521 so as to provide an increased surface area for glue adhesion, when mouth piece 501 is glued into top groove 512 of sleeve 511 during assembly. It is noted that assist member 521 is positioned between outer air passage openings 522 and an inner partial ring including projecting keys 518 as will be discussed. As will be shown, this inner partial ring bounds the oxygen flow and guides such flow to inner openings 523. It is noted here, that ambient air flow A passes between knob member 506 and the bottom arcuate curve of rim 525 on mouthpiece member 501.

As seen best in FIG. 5, an inner web supports respective undulations 516 during formation, and joins an inner bounded receiving opening 519 for receiving sleeve 511 during assembly. A keyed web portion or joining web 520 projects from the perimeter of bounded receiving opening 519 to support a valve central opening 515 for receiving valve stem member 504A. A bottom view of bottle mounting member 503 notes the positioning of outer skirt member 513 relative to sleeve 511 bounding an inner base passage 509. An inner skirt member 514 project in a step-wise fashion and forms openings 505 for optional ambient air transmission. Opposing sets of stabilizing members 524 project inwardly into inner base passage 509 of sleeve portion 511 and serve to guidably receive and slidably guide central member 517, as will be shown.

In an optional means for joining bottle mounting member 503 to a top of bottle or canister 502, a plurality of double-sided sticky adhesive 507 may be positioned inwardly of air passage openings 505 for adhering to the bounded contact region defined between bottle boss member 508 and valve stem support 504.

As is noted in FIG. 7, inward stabilizing members 524 project inwardly for guiding central stem 517 of action knob 506. Stabilizing members 524 also join proximate their respective top portions in inner base passage 509 forming angular semi-triangular pointed projections for receiving portions of action knob as will be shown. Stabilizing members 524 also bound respective inner regions between them so as to guide valve stem member 504A without causing undue contact. As should be realized now, joining web 520 action knob 506 is assembled by sliding it on top of sleeve 511 in so that web 520 rests between respective stabilizing members 524 on either side of inner base passage 509, thereby allowing the present assembly to be assembled in either of two positions, both equally effective to down-stream operation, thereby speeding assembly time.

Figure 9:
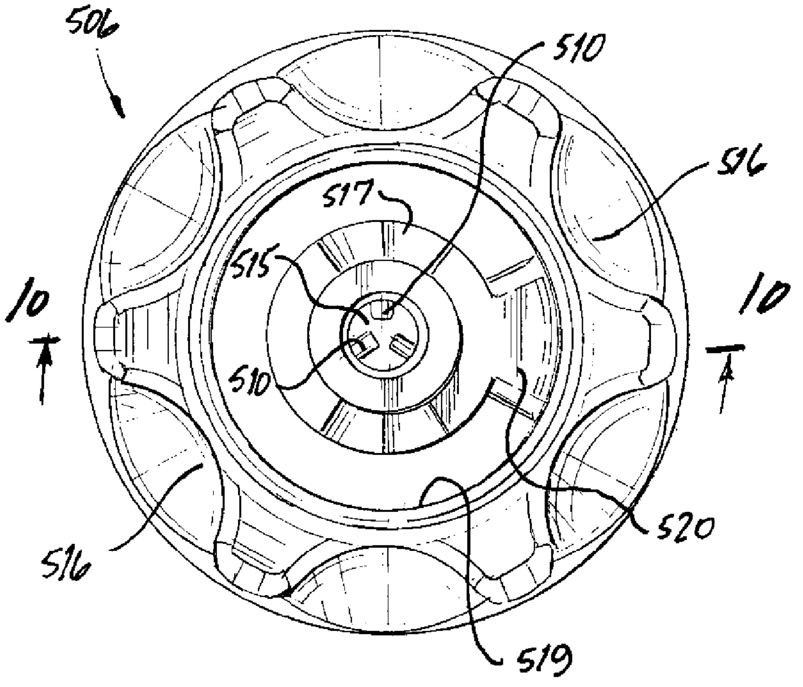
FIG. 9 is a top view of an action knob according to the present invention.
Figure 10:
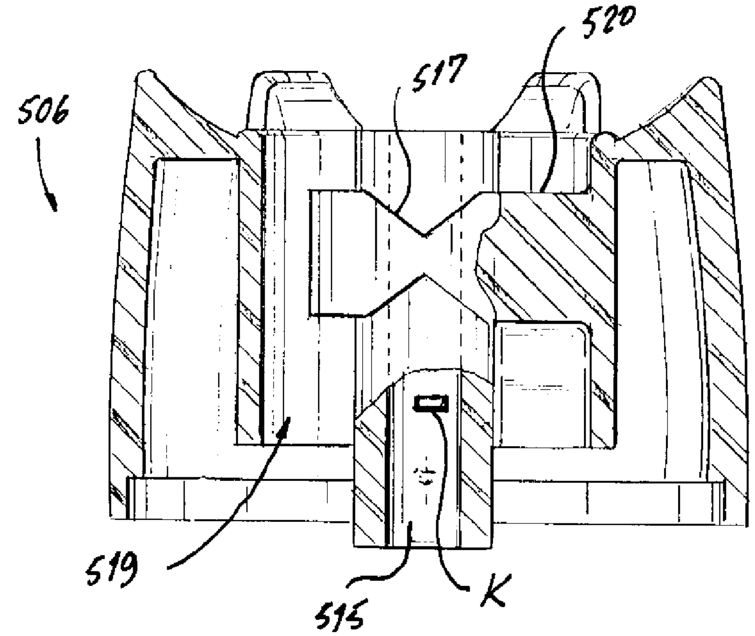
FIG. 10 is a sectional view along line 10-10 in FIG. 9.

Referring now to FIGS. 9 and 10, action knob member 506 is shown with bounded central opening 515 receiving three off-set and inwardly projecting actuation urging studs 510, 510, 510, as shown. During assembly, actuation urging studs 510 (a tip end of one is shown at K in FIG. 10), contact the top of valve stem member 504A, and upon actuation pivot with action knob 506 and move downwardly to release oxygen. Also shown are two respective receiving regions on sloped edges or receiving keyways formed in 517 proximate parallel sides of web 520. As will be later shown, receiving regions receive respectively keys 518 from mouthpiece 501, and the upwardly sloped key formed from joined stabilizing members 424, 424.

Figure 11:
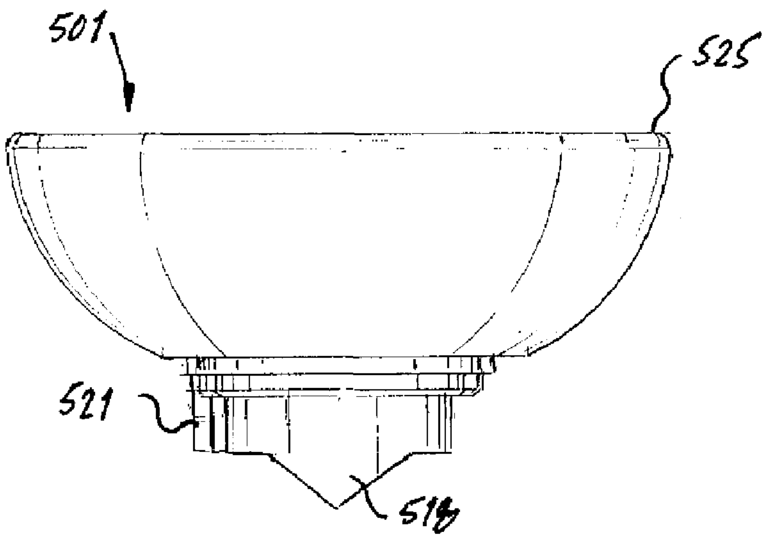
FIG. 11 is a side view of a mouth piece according to the present invention.
Figure 12:
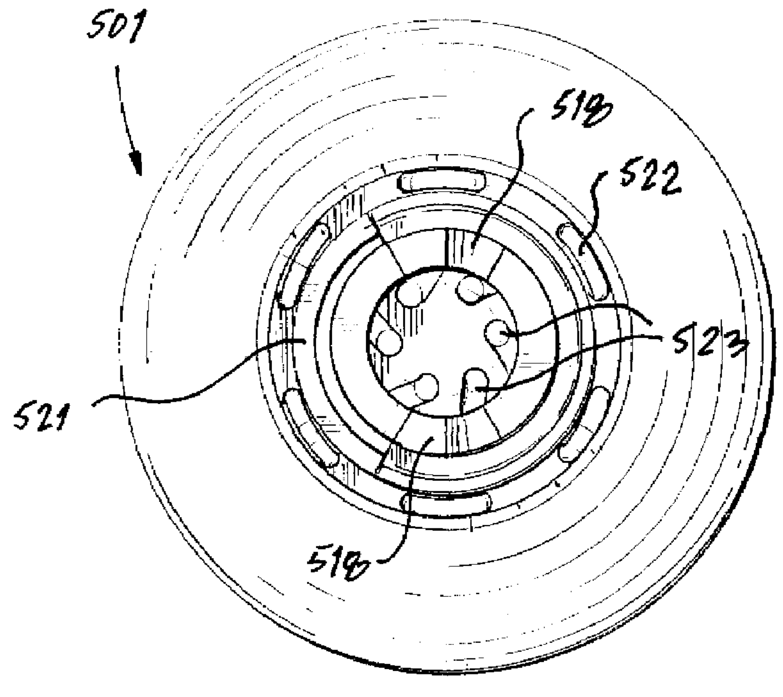
FIG. 12 is a bottom view of the mouth piece in FIG. 11.

Referring now to FIGS. 11 and 12, mouthpiece member 501 includes two opposing keys 518 as shown that fit within respective keyways 517 in action knob 506. FIG. 12 notes particularly the relationship between outer openings 522, inner openings 523, and glue member 521 there between completing the gap noted in sleeve 511 during assembly to provide a secure engagement to resist lift under rotational movement.

Figure 14:
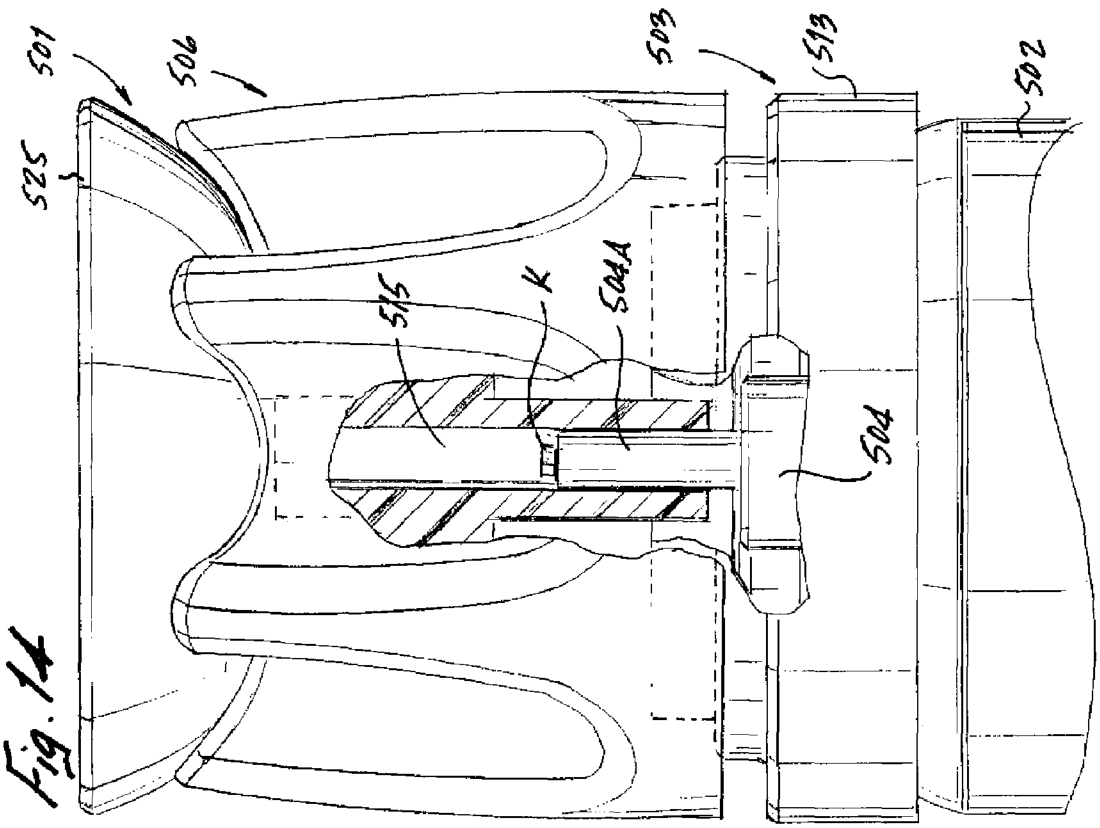
FIG. 14 is partially cut-away assembled view of FIG. 13 noting valve positioning.
Figure 13:
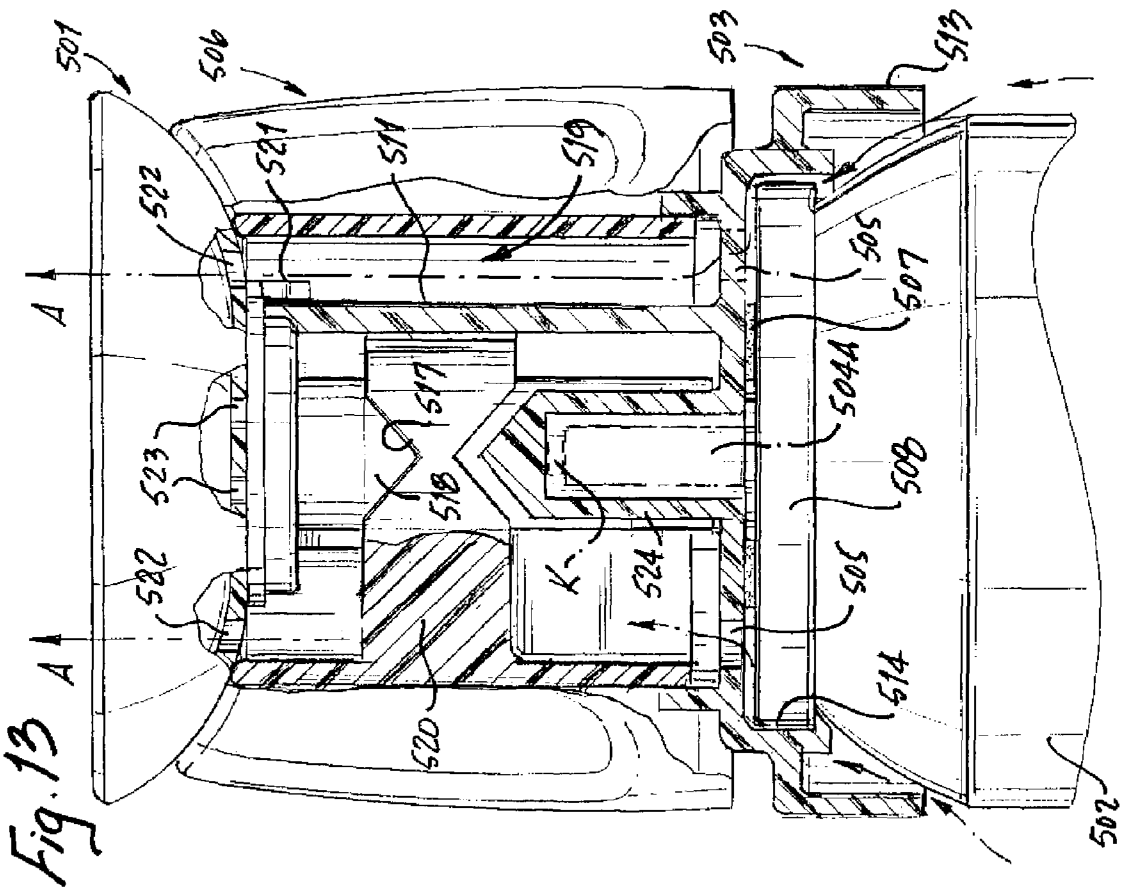
FIG. 13 is a partially cut-away assembled view of the present invention in a closed condition.

Referring now to FIGS. 13 and 14, apparatus or assembly 500 is shown in an at-reset, or non-actuated condition with the top of urging studs 510 (the end shown at letter K in section) resting upon the top surface of stem member 504A. Inner skirt 514 is shown with a snap engagement lip at its bottom edge for snap-engaging boss 508 of canister or bottle 102 and effecting a secure attachment thereto. Inner skirt 514 and it's snap engagement lip are spaced from urging studs 510 so that upon a user first assembly step (fixing bottle mounting member or can adaptor 503 onto can 502, there are no pressures or stresses on stem member 504A which is securely and slidably guided between respective sides of stabilizing members 524 (See FIG. 14) so that its movement along the can axis is not deflected. As seen, keys 518 are centrally located within top open keyway or sloped joint formed by slopes 517 on web 520 on the top or mouthpiece-side, so that respective keys formed by joined stabilizing members 524 are not in contact with web 520.

As shown, are optional adhesive tape members 507 for fixing (optionally) can adaptor 503 to can 502. As should be noted, the outer rim 525 of mouthpiece 501 slopes downwardly to meet with the sealing upward curve of the top of undulations 516. Also noted is the alignment of inner openings 523 with inner base passage 509 for the transmission of oxygen along the central opening 515. Similarly shown is the engagement (fixed) of glue member 521, fixed by adhesive, sonic welding or other conventional means, to sleeve member 511, thereby pivotably engaging action knob 506 there between.

Figures 15, 16:
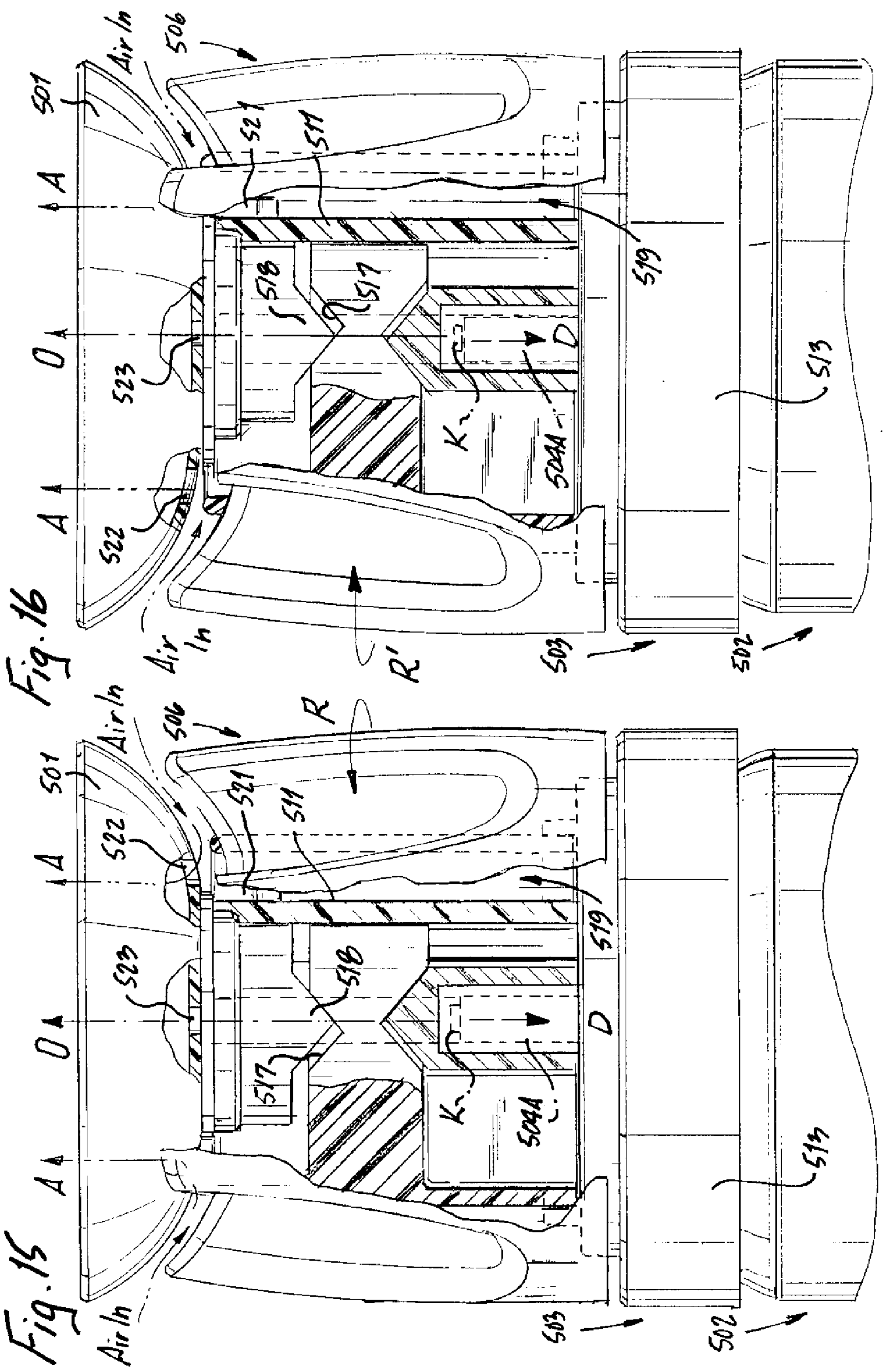
FIG. 15 is a partially cut-away assembled view of the present invention in an open or use condition.
FIG. 16 is a partially cut-away assembled view of FIG. 15 noting valve actuation for use.

Turning now, specifically to FIGS. 15 and 16, two directions R, R' are noted about a central pivot axis which is the same as the axis of assembly 100. During rotation in either direction, slopes 517 slide along sloped sides of keys 518 toward initial engagement with corresponding sloped sides of joined stabilizing members 524. As a consequence of the constructions, with action knob 506 pivotably joined between the fixed-in-position mouth piece 501 and can adaptor 503, during rotation in either direction R, R', action knob 506 moves axially toward can 502, placing pressure on upwardly urged stem 504A via urging studs 510 that ravel rotationally and downwardly to release oxygen. As can be seen from the corresponding views of either rotational direction, movement in either direction places downward pressure on valve stem 504A to release oxygen flow while simultaneously spacing to top of undulations 516 from the outer curve of mouthpiece 501, thereby allowing atmospheric air flows A, to enter along mouthpiece 501, into outer holes 522, to mix with oxygen and supply sufficient lung volume to satisfy a user while minimizing the risk of oxygen poisoning through blood over saturation. It should be noted, that in an alternative construction, minimizing web thickness 520 so that the respective tips of keys 518 are positioned such that the upward elastic urging of stem member 504A, is resisted by the rotational resistance of action knob 506, that the present assembly 500 includes a mechanism for hands free use so that oxygen and air flow will continue without the continuous user-manipulation of action knob 506. As can also be seen in reviewing the contrasts between respective non-use views FIGS. 13-14, and in-use views FIGS. 15-16, the present invention enables a mechanism for entraining atmospheric air in a delivered oxygen stream while allowing a responsive hands free use.

Figure 17:
FIG. 17 is a perspective view of the present invention in use.

Referring now to FIG. 17, a user 1000 is positioning assembly 500 for rapid one-handed use. As can be seen, a single hand action to rotate in either direction R/R' thereby improving a user-security during high risk or high activity sports such as climbing. For the reasons noted above, a hands-free use mechanism is provided that enables the turn of knob 506 and later use without continual pressure, thereby allowing a user rest in a prone position with mouthpiece 501 in close proximity to their lips thus minimizing damage and pain from pressure against chapped lips or where a user is injured.

In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. An assistive breathing apparatus for personal use by a user, comprising:

a bottle mounting member;

means for securely mounting said bottle mounting member about a valve assembly of an external bottle, said external bottle having a bottle axis and containing a use-gas;

a mouthpiece member mounted on said bottle mounting member;

an action knob pivotally mounted between said bottle mounting member and said mouthpiece member;

means for entraining an external atmosphere within a release volume of said use-gas during said use; and means for actuating said valve assembly upon a rotation of said action knob by said user about said bottle axis; and said means for actuating said valve assembly includes dual rotation means for enabling a rotation of said action knob in either direction about said bottle axis from a non-actuation position to respective dual use positions, thereby improving a user convenience of said apparatus.

2. An assistive breathing apparatus, according to claim 1, wherein:

said means for securely mounting further comprising:

at least one of a means for snap-mounting said bottle mounting member on said bottle and an adhesive joining means for adhering said mounting member on said bottle without actuating said valve assembly.

3. An assistive breathing apparatus, according to claim 2, wherein:

said breathing apparatus includes said means for snap-mounting, and said means for snap-mounting further comprises:

at least a first snap link member for snap engaging a rim of said bottle.

4. An assistive breathing apparatus, according to claim 2, wherein:

said breathing apparatus includes said means for snap-mounting, and said means for snap-mounting further comprises:

at least said adhesive joining means for adhering.

5. An assistive breathing apparatus, according to claim 2, wherein:

said breathing apparatus includes said means for snap-mounting, and said means for snap-mounting includes both said at least a first snap link member for snap engaging a rim of said bottle and said adhesive joining means for mounting.

6. An assistive breathing apparatus, according to claim 1, further comprising:

means for retaining said valve assembly of said bottle in an in-use hands-free actuation position following said rotation, thereby allowing said apparatus to have an improved user convenience.

7. An assistive breathing apparatus, according to claim 1, wherein:

said means for actuating said valve further comprises:

means for bounding and stabilizing a valve stem of said valve assembly during an actuation, whereby said means for bounding and stabilizing minimize a misalignment of said valve stem and damage to said valve assembly.

8. An assistive breathing apparatus, according to claim 1, further comprising:

a plurality of air passages in said mouth piece member;

a first portion of said air passages transmitting said use-gas to said user during a personal use; and a second portion of said air passages transmitting said entrained atmosphere to said user from said means for entraining, whereby during said use said user inhales both said use-gas and said entrained atmosphere.

9. An assistive breathing apparatus, according to claim 8, further comprising:

means for guiding said use-gas from said valve assembly to said first portion of said air passages during a use, whereby said means for guiding aids a transportation of said use-gas to said user.

10. An assistive breathing apparatus, according to claim 1, further comprising:

means for sealing said means for entraining said external atmosphere following said use, whereby said means for sealing positions said action knob in close proximity to said mouthpiece member.

11. An assistive breathing apparatus, according to claim 9, further comprising:

a plurality of gripping aids proximate a periphery of said action knob, whereby said gripping aids improve a user-grip of said action knob during said use.

12. An assistive breathing apparatus, according to claim 1, further comprising:

means for sealing said means for entraining said external atmosphere following said use, said means for sealing further comprising:

a convex curved sealing surface on said mouthpiece member, and a concaved sealing surface on said action knob, whereby said mouthpiece member nests within said action knob and said action knob moves relative to said concaved sealing surface during said rotation and use.

13. A method for assembling an assistive breathing apparatus, comprising the steps of:

providing a bottle having a bottle axis and containing a use-gas;

providing a bottle mounting member;

securing said bottle mounting member about a valve assembly of said bottle;

positioning an action knob about a portion of said bottle mounting member;

securing a mouthpiece member on said bottle mounting member, thereby enabling a relative rotation of said action knob relative to both said bottle mounting member and said mouthpiece member;

entraining an external atmosphere within a release volume of said use-gas during said use; providing said valve assembly with dual rotation means; and enabling a rotation of said action knob in either direction about said bottle axis from a non-actuation position to respective dual use positions, thereby improving a user convenience of said apparatus.

14. A method for assembling an assistive breathing apparatus according to claim 13, further comprising the step of providing a means for actuating a valve assembly of said bottle upon a rotation of said action knob by said user to release said use-gas.

15. A method for assembling an assistive breathing apparatus, according to claim 13, wherein:

said step of securing said bottle mounting member includes a step of snap-engaging said bottle mounting member with a rim of said bottle; whereby a positive snap-fit secures said bottle mounting member to said bottle.

16. A supply container for a use gas, said supply container comprising:

a bottle for containing a use-gas, said bottle having a bottle axis and including a valve assembly, said valve assembly including a valve stem a bottle mounting member;

means for securely mounting said bottle mounting member to said bottle and about said valve assembly;

an action knob mounted to said bottle mounting member for pivoting movement thereon;

plate means disposed at a top of said action knob, said plate means being affixed to said bottle mounting member, said plate means normally being engaged on top of said action knob in contact therewith, said action knob being supported such as to be moveable downwardly relatively of said plate means during an actuation thereof leaving a space gap between said action knob and said plate means;

said action knob and said bottle mounting means carrying cooperating structure operable upon a user rotation of said action knob about said bottle axis for actuating said valve stem and effecting a release of use gas from said bottle;

said means for actuating said valve assembly includes dual rotation means for enabling a rotation of said action knob in either direction about said bottle axis from a non-actuation position to respective dual use positions thereby improving a user convenience of said supply container;

said plate means including a first set of openings disposed centrally of said plate means through which said released gas outflows, said plate means including a second set of openings circularly spaced outwardly of said first set of openings;

means for entraining an external atmosphere within a release volume of said use-gas during said use; and released gas flow through said first set of openings being effective to induce an inflow of any outside environment gas presence into said space gap and through said second set of openings.

17. A supply container in accordance with claim 16, wherein said action knob and said bottle mounting means further embodying structure defining flow passages axially aligned with said second set of openings for additional inducement of outside environment gas presence through said plate means.

18. A supply container for a use-gas, said supply container comprising:

a bottle for containing a use-gas, said bottle having a bottle axis and including a valve assembly, said valve assembly including a valve stem;

a bottle mounting member;

means for securely mounting said mounting member to said bottle and about said valve assembly;

means for entraining an external atmosphere within a release volume of said use-gas during said use;

an action knob mounted to said mounting member for pivoting movement thereon; and means for actuating said valve assembly upon a user rotation of said action knob about said bottle axis for effecting a release of use-gas from said bottle through said valve stem, wherein said means for actuating said valve assembly includes dual rotation means for enabling a rotation of said action knob in either direction about said bottle axis from a non-actuation position to respective dual use positions thereby improving a user convenience of said supply container.

19. A supply container in accordance with claim 18, wherein:

said means for actuating said valve assembly includes dual rotation means for enabling a rotation of said action knob in either direction about said bottle axis from a non-actuation position to respective dual use positions thereby improving a user convenience of said supply container.

20. A supply container in accordance with claim 18, wherein:

said means for actuating said valve further comprises:

means for bounding and stabilizing said valve stem of said valve assembly during an actuation, whereby said means for bounding and stabilizing minimize a misalignment of said valve stem and damage to said valve assembly.

21. A supply container in accordance with claim 18, further comprising:

a plurality of gripping aids proximate a periphery of said action knob, whereby said gripping aids improve a user-grip of said action knob during a supply container use.

* * * * *